United States Patent [19]
Zeff et al.

[11] 4,195,623
[45] Apr. 1, 1980

[54] PARALLEL AORTA BALLOON PUMP AND METHOD OF USING SAME

[76] Inventors: Robert H. Zeff, 4220 Foster Dr.; Steven J. Phillips, 6023 N. Waterbury Rd., both of Des Moines, Iowa 50312

[21] Appl. No.: 817,728

[22] Filed: Jul. 21, 1977

[51] Int. Cl.² .................. A61F 1/24; A61M 1/03; F04B 9/12
[52] U.S. Cl. .................. 128/1 D; 128/273; 3/1.7; 417/384
[58] Field of Search .................. 128/1 D, 214 R, 273, 128/DIG. 3; 417/474, 479, 384; 3/1.7

[56] References Cited

U.S. PATENT DOCUMENTS

| | | |
|---|---|---|
| 3,409,913 | 11/1968 | Kantrowitz et al. ........ 128/334 C X |
| 4,015,590 | 4/1977 | Normann ............... 128/1 D |
| 4,034,742 | 7/1977 | Thoma ................. 128/1 D |
| 4,051,840 | 10/1977 | Kantrowitz et al. ........ 128/1 D |
| 4,080,958 | 3/1978 | Bregman et al. .......... 128/1 D |
| 4,116,589 | 9/1978 | Rishton ............... 128/1 D X |

OTHER PUBLICATIONS

Jama, vol. 187, #6, Feb. 8, 1964, pp. 29-33.
Jama, vol. 193, #10, Sep. 1965, pp. 25-30.

Primary Examiner—Dalton L. Truluck
Attorney, Agent, or Firm—Zarley, McKee, Thomte, Voorhees & Sease

[57] ABSTRACT

A parallel aorta passageway is provided with its upper end being connected to the aorta in close proximity to the heart. The opposite ends of the parallel aorta are grafted to the aorta without interrupting the blood flow through the heart and circulatory system. The parallel aorta is received in an outer tube with a balloon being positioned between the inner and outer tubes. An air line extends from the lower end of the balloon through the ribs under the flesh and out of the body through a hole drilled in the iliac crest. The tube is connected to an external control unit synchronized with the heart to provide counter pulsations 180° out of phase with the heart pulsations.

26 Claims, 6 Drawing Figures

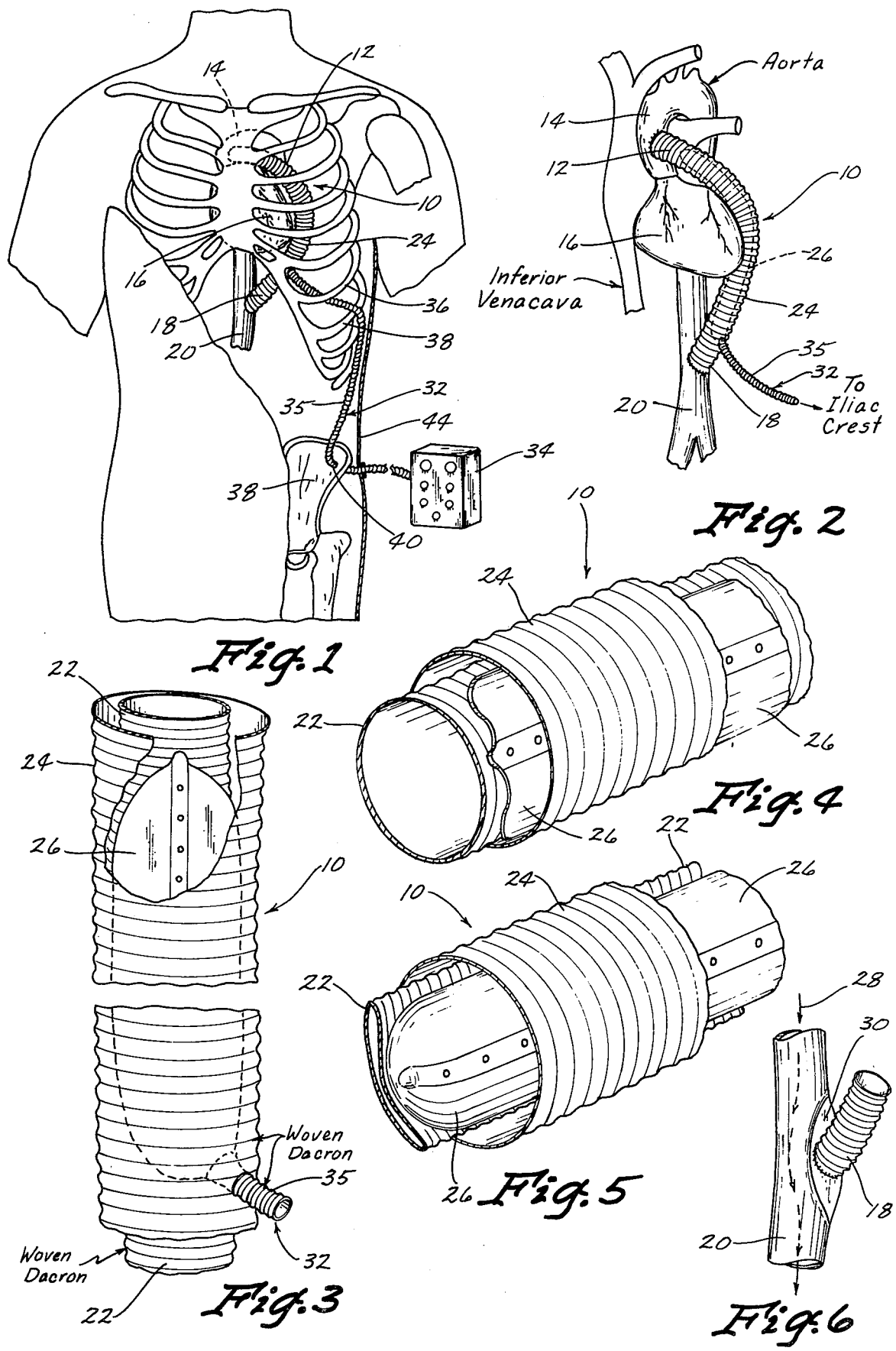

PARALLEL AORTA BALLOON PUMP AND METHOD OF USING SAME

BACKGROUND OF THE INVENTION

Assisted circulation techniques are an outgrowth of extracorporeal pump oxygenated systems developed in the mid-1950's. These techniques have been applied to patents for temporary assisted circulation, and more recently, for permanent left ventricular assistance. Most of the experimental and clinical application of these assist devices are based on the principle of diastolic augmentation. This is a system of counterpulsation where an external energy source delivers a pulsatile wave into the central circulation during cardiac diastole, and relaxes during cardiac systole. This is done by timing with the patient's electrocardiogram or pressure wave form.

This allows the following:
1. The stroke volume per unit work of the left ventricle is increased.
2. The diastolic perfusion pressure and ratio of mean diastolic pressure to mean systolic pressure is increased.
3. Coronary flow increases preferentially with diastolic pressure since coronary vascular resistance is minimal during cardiac diastole.
4. Coronary collateral flow to ischemic region of the myocardium is increased.
5. The modification of pulse pressure distribution in the aorta favors the increase of flow to vital organs.

This principle has been applied since the mid-1960's as a temporary form of cardiac assistance for patients in acute heart failure with a commercially available intra-aortic balloon pump.

A permanent booster heart, based on the principles described above should have the following features:
1. Effective hemodynamic support for the failing left ventricle.
2. Be designed so that intermittent as well as continuous use can be achieved.
3. Be failure free over long periods.
4. Have a size and shape that interfer minimally with other organs.
5. Be constructed of biologically compatible materials.
6. Be implanted with a tolerable surgical risk.
7. Be controlled reliably under varying physiologic conditions.
8. Have a portable power source to allow the patient free movement.
9. The transcutaneous connector should be constructed in such a way to facilitate easy connection to the power source with minimal risk of infection.

Some attempts at implantation of a permanent left ventricular assist device over the past 10-12 years have met with limited success. The pioneer in this field is, Dr. Adrian Kantrowitz, who implanted (in 1965 and 1966) a mechanical U-shaped auxiliary ventricle in two patients. Problems occurred with synchronization and clotting in these patients. In 1970 through 1972, again under Dr. Adrian Kantrowitz, Dr. Steven Phillips did some definitive experimental work with the hemodynamic effects of a dynamic aortic patch in animals and, with Kantrowitz, implanted two such devices in patients. One patient did not survive the surgery. The second survived but died of infection a few months later that occurred via the transcutaneous connector. A third attempt in 1976 by Dr. Kantrowitz to implant another device was only successful short-term as the patient also died of ascending infection from the transcutaneous connector.

These above devices of Kantrowitz were implanted with utilization of the heart-lung machine and were based on the principle of diastolic augmentation. A transcutaneous connector required a skin button that ultimately caused the patients demise due to ascending infection.

SUMMARY OF THE INVENTION

In 1977 at Mercy Hospital, Des Moines, Iowa, Dr. Steven J. Phillips and Dr. Robert H. Zeff implanted a permanent left ventricular assist device in a patient. This device was implanted without the use of extra-corporeal circulation and utilized existing materials that are commercially available for human implantation. The device itself consists of a woven Dacron graft on the outside of which is mounted a pumping chamber. This entire system again is covered with a woven Dacron graft. The proximal end of the graft is sewn to an incision made in the ascending aorta and the distal end of the graft is sewn to an incision made in the distal descending thoracic aorta. The transcutaneous connecting tube is wrapped in Dacron Velour material and is tunneled through the chest wall through the subcutaneous tissues of the trunk, is brought out through a hole drilled in the iliac crest to the skin where it is connected to the extra-corporeal power driving source.

The stroke volume of this pulsatile aortic chamber is 30-45 cc. The diameter and pumping chamber sizes of this booster heart will vary with the size of the patient and the stroke volume desired.

Its advantages are as follows:
1. Implantation does not require use of extra-corporeal circulation.
2. Materials used have all been demonstrated to be biocompatible and certified for non-experimental or frequent clinical human use.
3. It is felt the major risk of any permanent left ventricular assist device is ascending infection through the transcutaneous connector.

By passing the transcutaneous connector through bone it is felt that the risk of infection is significantly reduced to the point that should allow long-term survival of the patient. This is because: (1) the bone fixes the tube in place, reducing its motion of tissue irritation; and (2) resists ascending infection by nature of its physiology. The transcutaneous connector in this case, as not in the cases of previously implanted permanent devices, is much smaller and of biocompatible material.

The physiology of the patient in chronic left ventricular failure is as follows. The normal stroke volume of the left ventricle is approximately 80 cc. Cardiac reserve is such that chronic left heart failure does not occur until that stroke volume falls to the range of 40-50 cc. It is felt that if 30-40 cc stroke volume can be added to the patient by an external power source then theoretic recovery function can occur. A permanent left ventricular assist device as described can do this. By adding a 30-40 cc stroke volume to a patient in chronic failure, the patient should be allowed to return to a more normal function. Continuous pumping is not necessary. Intermittent pumping for a few hours a day and eventually a few days a week should be enough to allow the patient to remain in a clinically healthy state. This concept is similar to the concept of renal dialysis where a patient who has no functioning kidneys can be periodically and intermittently hooked up to a kidney machine. Between these hookups the patients can return to a more normal life. This can be the case with an artificial booster heart. Portable pumping as well as hospital, home and intermittent treatments can be carried to allow the patient to remain in a physiologic healthy state.

DESCRIPTION OF THE DRAWINGS

FIG. 1 is a front elevational view of the permanent left ventricular device implanted in the body.

FIG. 2 is an enlarged fragmentary view of the heart and aorta connected to the ventricular assist device.

FIG. 3 is an enlarged view of the parallel inner and outer aorta tubes having an inflatable balloon therebetween.

FIG. 4 is a view similar to FIG. 3 showing the balloon in its deflated condition.

FIG. 5 is a view similar to FIG. 4 showing the balloon inflated with the intertube substantially collapsed.

FIG. 6 is an enlarged view of the air tube grafted to the aorta while blood continues to flow therethrough.

DESCRIPTION OF THE PREFERRED EMBODIMENT

The parallel aorta balloon pump is generally referred to in FIG. 1 by the reference numeral 10 and is shown in FIG. 2 connected at its upper end 12 to the ascending aorta 14 in close proximity to the heart 16 while the lower end 18 is connected to the descending thoracic aorta 20. The balloon pump 10, as seen in FIG. 3, includes an inner tube 22 and an outer tube 24 between which an inflatable balloon 26 is positioned. The opposite ends of the tubes 22 and 24 are grafted to the aorta, as seen in FIG. 6, wherein the end 18 is grafted to the descending thoracic aorta 20 while blood continues to flow through the aorta as indicated by the arrows 28. A small fold 30 is made in the aorta 20 and an opening is formed only sufficiently large to accommodate the grafting of the tube ends thereto. Flow of blood through the aorta 20 is not impaired during this grafting procedure and thus a lung and heart machine is not required for this operation.

The tubes 22 and 24 are formed from biocompatible material such as woven Dacron Velour material available from U.S. Catheter, Instruments of America, Ithaca, New York. An intra-aortic balloon pump may be purchased from Datascope Corporation, Paramus, New Jersey.

The balloon 26 is connected by an inner tube 32 to a control unit 34 outside the body. The tube 32 is also wrapped with woven Dacron 35 and thus provides a biocompatible material in contact with body tissue. As seen in FIG. 1, the tube 32 extends between the ribs 36 and 38 downwardly to the iliac crest 40 where the tube exits through a hole 42 at the iliac crest. This routing of the tube 32 assures that it is held firmly minimizing irritation and possible infection to the body. The tube 60 exits from the body at a point where there is minimum flesh as there is substantially only skin 44 over the iliac crest at the point where the tube 32 exits from the body. The bone in the iliac crest cannot become infected and thus risk of infection around the tube is substantially eliminated.

In FIGS. 4 and 5 the balloon 26 is shown in the deflated and inflated conditions, respectively. The control unit 34 is in turn connected to an inner source which synchronizes the pulsations of the pump 10 with the operation of the heart 16 such that they are 180° out of phase with each other. The blood pumped by the pump 10 will substantially move upwardly in the inner tube 22 towards the heart during cardiac distole. The pump 10 will be at rest during cardiac systole.

The inner and outer tubes 22 and 24 are approximately 16 to 18 inches long with the balloon 26 being approximately 14 inches in length. The inner tube 22 is 22 mm in diameter while the outer tube is approximately 25 mm. The balloon 26 has a diameter of approximately 12 mm. The flow capacity of the tube 22 should be approximately equal to the aorta. Air is introduced into the balloon 26 at the bottom end and thus inflates upwardly forcing blood upwardly towards the heart during each pulsation. The tubes 22 and 24 are substantially straight throughout their length in the sense that there are no sharp turns or volume variations thereby eliminating undesirable turbulence within the tube 22 or the aorta. The driving unit for supplying air to the heart pin, including the control unit 34, is available from Datascope Corporation, Paramus, New Jersey.

We claim:

1. An implantable parallel aorta balloon pump for pumping blood from the descending aorta to the ascending aorta comprising, a valveless open flexible substantially straight inner tube positioned in a flexible substantially straight outer tube, connecting means on the one end of said inner tube for connecting said one end to a descending aorta, connecting means on the other end of said inner tube for connecting said other end to an ascending aorta, a balloon positioned between the walls of the inner and outer tubes for engagement against only one side of the inner tube wall, and said balloon having one end adjacent said one end of said inner tube and an opposite end positioned adjacent the other end of said inner tube, an air drive means connected to said one end of said balloon alternately inflating and deflating said balloon whereby said one side of the inner tube wall is collapsed when said balloon is inflated thereby providing a pumping action in said inner tube in direction towards the other end of said balloon to move blood from said one end of said inner tube to the other end of said inner tube.

2. The structure of claim 1 wherein said inner and outer tubes are made of woven Dacron material.

3. The structure of claim 2 wherein said air drive means connected to said balloon is connected by a tube wrapped in Dacron Velour material.

4. A method of assisting the heart comprising the steps of, implanting in the body without interrupting the flow of blood through the heart and its circulation system a balloon pump including a substantially straight open and flexible passageway parallel to and connected between the ascending aorta and descending aorta and positioning an inflatable balloon on one outside wall of the parallel passageway and providing a flexible outer tube on an inner tube with the balloon therebetween, connecting an external gas drive means to the pump and extending a tube from the lower end of the balloon to outside the body, and synchronizing the pumping action to provide pulsations 180° out of phase with the heart thereby producing upwardly moving pressure waves in the parallel passageway as the balloon fills from the lower end to the upper end.

5. The method of claim 4 wherein the step of connecting a drive means to the pump is further defined as connecting an external air source to the pump.

6. The method of claim 5 wherein the step of connecting an external air source to the pump is further defined by extending a tube from the balloon to outside the body through a bone in close proximity to an outer body skin.

7. The method of claim 6 wherein the step of extending the tube through a bone is further defined as extending the tube through the iliac crest.

8. The method of claim 6 wherein the step of extending a tube from the balloon to the outside of the body through a bone in close proximity to an outer body skin is further defined to include wrapping the tube in a biocompatible Dacron Velour material.

9. The method of claim 4 wherein the step of providing a passageway parallel to the aorta is further defined as providing a passageway having a volume capacity substantially equal to the aorta.

10. The method of claim 4 wherein the step of synchronizing the pumping action is further defined as providing a pumping action of approximately 30–45 cc.

11. The method of claim 4 wherein the step of connecting opposite ends of the passageway to the aorta is further defined as grafting a tube of woven Dacron material to the aorta.

12. The method of claim 11 wherein the step of grafting opposite ends of a tube to the aorta is further defined as providing incisions in the aorta no larger in size than is necessary to provide unrestricted flow into the tube passageway.

13. A method of assisting the heart comprising the steps of,
providing a passageway parallel to and connected at opposite ends to the aorta and positioning an inflatable balloon on the outside wall of the parallel passageway and providing an outer tube on an inner tube providing the passageway with the balloon therebetween,
connecting a pump operatively to the parallel passageway,
connecting an external air source drive means to the pump and extending a tube from the balloon to outside the body through a bone in close proximity to an outer body skin, and
synchronizing the pumping action to provide pulsations 180° out of phase with the heart.

14. The method of claim 13 wherein the step of extending the tube through a bone is further defined as extending the tube through the iliac crest.

15. The method of claim 14 wherein the step of connecting a passageway to the aorta is further defined by connecting the upper end to the aorta in close proximity to the heart.

16. The method of claim 15 wherein the step of providing a passageway parallel to the aorta is further defined as providing a passageway having a volume capacity substantially equal to the aorta.

17. The method of claim 15 wherein the step of synchronizing the pumping action is further defined as providing a pumping action of approximately 30–45 cc.

18. The method of claim 15 wherein the step of connecting opposite ends of the passageway to the aorta is further defined as grafting a tube of woven Dacron material to the aorta.

19. The method of claim 18 wherein the step of grafting opposite ends of a tube to the aorta is further defined as providing incisions in the aorta no larger in size than is necessary to provide unrestricted flow into the tube passageway.

20. The method of claim 13 wherein the step of connecting the opposite ends of the passageway to the aorta is performed without interrupting the flow of blood through the heart and its circulatory system.

21. The method of claim 13 wherein the step of extending a tube from the balloon to the outside of the body through a bone in close proximity to an outer body skin is further defined to include wrapping the tube in a biocompatible Dacron Velour material.

22. A method of assisting the heart comprising the steps of,
implanting a balloon pump in the body,
connecting a gas drive means to the pump, and
connecting an external gas source to the pump by extending a tube from the pump to outside the body through a bone in close proximity to an outer body skin.

23. The method of claim 22 wherein the step of extending the tube through a bone is further defined as extending the tube through the iliac crest.

24. The method of claim 22 wherein the step of implanting the balloon pump is further defined as connecting the inlet to the descending aorta and the outlet to the ascending aorta.

25. The method of claim 24 and further providing the balloon pump as a substantially straight and open passageway parallel to the aorta and having substantially equal volume capacity with the inlet and outlet having tubes grafted to the aorta by providing incisions in the aorta no larger in size than is necessary to provide unrestricted flow into the tube passageway and without interrupting the flow of blood through the heart and its circulatory system.

26. The method of claim 25 wherein the pumping by the balloon pump is further defined by compressing one side only of the passageway and introducing gas into the balloon at one end adjacent the inlet end of the passageway.

* * * * *